(12) United States Patent
Cheng et al.

(10) Patent No.: US 8,551,735 B2
(45) Date of Patent: Oct. 8, 2013

(54) METHOD OF DIAGNOSING GASTRIC CANCER BY USING HUMAN NEUTROPHIL PEPTIDE 1-3

(75) Inventors: Chun-Chia Cheng, Taipei County (TW); Shui-Cheng Lee, Taoyuan County (TW)

(73) Assignee: Atomic Energy Council—Institute of Nuclear Energy Research, Lungtan, Taoyuan (TW)

( * ) Notice: Subject to any disclaimer, the term of this patent is extended or adjusted under 35 U.S.C. 154(b) by 367 days.

(21) Appl. No.: 12/942,126

(22) Filed: Nov. 9, 2010

(65) Prior Publication Data
US 2012/0115178 A1    May 10, 2012

(51) Int. Cl.
*C12P 21/04* (2006.01)

(52) U.S. Cl.
USPC .................................. 435/69.6; 313/564

(58) Field of Classification Search
USPC .................................. 313/564; 435/69.6
See application file for complete search history.

(56) References Cited

PUBLICATIONS

Isomoto et al. "Elevated concentrations of alpha-defensins in gastric juice of patients with *Helicobacter pylori* infection", American J of Gasteroenterology, 2004, 99:1916-1923.*

Mohri et al "Identification of macrophage migration inhibitory factor and human neutrophil peptides 1-3 as potential biomarkers of gastric cancer", British J of Cancer, 2009, published online Jun. 23, 101:295-302.*

Wehder et al. "Depicting the spatial distribution of proteins in human tumor tissue combining SELDI and MALDI imaging and immunohistochemistry", J of Histochemistry & Cytochemistry, 2010, 58(10):929-937.*

* cited by examiner

*Primary Examiner* — Bin Shen
(74) *Attorney, Agent, or Firm* — Jackson IPG PLLC (57) ABSTRACT

Human neutrophil peptide (HNP) 1-3, used as diagnostic and therapeutic molecular probes, are found in clinical tissues of gastric cancer patients. In the analytical process according to the present disclosure, pairs of gastric cancer tissues are used to seek the putative biomarkers by proteomic strategy based on matrix assisted laser desorption ionization-imaging mass spectrometry (MALDI-IMS). Then, three differential biomarkers, including HNP-1, -2 and -3, are identified (P<0.001) and overexpressed in gastric cancer. At last, western blotting and immunohistochemistry are used to validate the protein expression in gastric cancer tissues. In conclusion, the use of the up-regulated proteins, HNP1-3, helps diagnosis and therapy in clinical for gastric cancer after validating the sensitivity and specificity.

3 Claims, 13 Drawing Sheets

HNP-1 : ACYCRIPACIAGERRYGTCIYQGRLWAICC
HNP-2 : CYCRIPACIAGERRYGTCIYQGRLWAICC
HNP-3 : DCYCRIPACIAGERRYGTCIYQGRLWAICC

METHOD OF DIAGNOSING GASTRIC CANCER BY USING HUMAN NEUTROPHIL PEPTIDE 1-3

TECHNICAL FIELD OF THE DISCLOSURE

The present disclosure relates to diagnosing gastric cancer; more particularly, relates to using HNP1-3 for diagnosing gastric cancer with specificity and sensitivity, where gastric cancer is thus diagnosed for treatment at an early stage.

DESCRIPTION OF THE RELATED ARTS

Generally, malignant tumor comes from differentiation of epithelium cells. These cells usually have sustained matrix consisting of blood vessels and connective tissues. Although some malignant tumors grow fast and some slow, most malignant tumors grow faster than tissue cells around them.

There are benign tumors and malignant tumors. Malignant tumors usually have the following characteristics: (1) They invade and destroy normal tissues around. (2) They may be transferred to lymph gland or other organ through lymph or blood vessel. (3) They may apt to anaplastic; or, they may have worse cell division. (4) Malignant tumor usually grows faster than benign tumor; and, within several weeks or months, they may grow big enough to humor tissues around.

Malignant tumor is usually diagnosed by the following symptoms: (1) Tumor cells usually have strange shapes and the shapes are very different to those of normal cells. (2) Malignant tumor usually has bigger cell nucleus and darker cytoplasm than normal cell. Further, its cell nucleus usually has big and obvious nucleolus. (3) Number of malignant tumor processing mitosis is greater than that of normal cells; and various giant macrophage are contained. (4) Number and arrangement of chromosome of malignant tumor may be wrong.

Incidence rate of malignant tumor in digestive system is about 25%, which is the highest in all human body organs. Gastric adenocarcinoma is the most common tissue of gastric cancer, about 70%. According to World Health Organization (WHO), gastric cancer has the fourth-position incidence rate and the second-position lethal rate in the world, which causes about 800 thousands death per year and whose 5-year survival rate is only inferior to liver cancer, pancreas cancer and esophagus cancer. A gastric cancer can be identified into an early cancer or an advance cancer according to how bad it damages stomach. The early cancer hurts surface of stomach lining only. The advance cancer may hurt submucosa, penetrate stomach wall or even be transferred to other organs. The early cancer usually does not have obvious symptoms. The advance cancer has the following symptoms: (1) gastric hemorrhage abiding with vomiting, relieving black bowels, dizzying head and blurring eyes; (2) continuous stomach ache; (3) pylorus choked by tumor cells resulting in abdominal distention and bad appetite; and (4) bad feeling on which organ the cancer cells are transferred to, if ever.

The 5-year survival rate of gastric cancer is only higher than those of liver cancer, pancreas cancer and esophagus cancer. If early diagnose and early treatment are made, the 5-year survival rate can reach above 90%. But, gastric cancer at the early stage has no obvious symptom. Hence, endoscopy is used with much time and labor spent, not to mention low desire for the public to accept the examination.

Noninvasive serum carcino embryonic antigen (CEA) examination is introduced. For example, mass spectrum image analysis for matrix assisted laser desorption ionization-time of flight mass spectrometer (MALDI-TOF MS) uses MALDI-TOF MS, a matrix sprayer (CHIP1000) and an analysis software (ClinProt) to analyze peptides and proteins having mass spectrums between 3 kDa and 30 kDa; and images of distributions and expressions of protein biomarkers are then obtained for qualification and quantification analyses.

Pretreatment of samples used in mass spectrum image analysis is very important. A good pretreatment obtains a result having a high quality, a high reliability and a high reproducibility. Furthermore, no other markers are necessary for imaging in the mass spectrum analysis; and, distribution and expression of protein biomarker in disease tissue can be shown very quickly.

Normal matrix includes 2,5-dihydroxybenzoic acid (DHB), α-Cyano-4-hydroxycinnamic acid (CHCA), Sinapic Acid (SA), Trihydroxyacetophenone monohydrate (THAP), 3-hydroxy picolinic acid (3-HPA), dihydroxyacetophenone (DHA) and 2,4-dinitrophenylhydrazine (2,4-DNPH). DHB is suitable for analyzing saccharide, small-molecule peptide and nucleotide; CHCA, for peptide and small-molecule compound; and, SA, for peptide and big-molecule protein. Matrix spray technology affects resolution and reproducibility of the image, including droplet deposition by hand, CHIP1000 chemical printer (ChIP), acoustic reagent multi-spotter, electrospray deposition and dry-coating. Among them, ChIP and acoustic reagent multi-spotter are the best. By using those technologies, matrix is evenly dotted on tissue for crystallization with protein to obtain biomarkers for identification.

Although noninvasive serum CEA examination can be used for cancer examination in digestive system, sensitivity and specificity to gastric cancer are not good enough. Hence, the prior arts do not fulfill all users' requests on actual use.

SUMMARY OF THE DISCLOSURE

The main purpose of the present disclosure is to use HNP1-3 for diagnosing gastric cancer with specificity and sensitivity, where gastric cancer is thus diagnosed for treatment at an early stage.

To achieve the above purpose, the present disclosure is a method of diagnosing gastric cancer by using HNP1-3, comprising steps of: (a) obtaining samples of a gastric cancer tissue and a normal gastric tissue; (b) obtaining a P value of the gastric cancer tissue and a P value of the normal gastric tissue and obtaining protein biomarkers having different expressions between the gastric cancer tissue and the normal gastric tissue; and (c) obtaining three protein biomarkers having different expressions between the gastric cancer tissue and the normal gastric tissue to be gastric cancer protein biomarkers, where the three protein biomarkers have P values smaller than 0.001; where the three protein biomarkers have molecular weights of 3370, 3442 and 3486, separately; and where the three protein biomarkers are identified as human neutrophil peptide 1-3. Accordingly, a novel method of diagnosing gastric cancer by using HNP1-3 is obtained.

BRIEF DESCRIPTIONS OF THE DRAWINGS

The present disclosure will be better understood from the following detailed description of the preferred embodiment according to the present disclosure, taken in conjunction with the accompanying drawings, in which.

DESCRIPTION OF THE PREFERRED EMBODIMENT

The following description of the preferred embodiment is provided to understand the features and the structures of the present disclosure.

Figure 1:
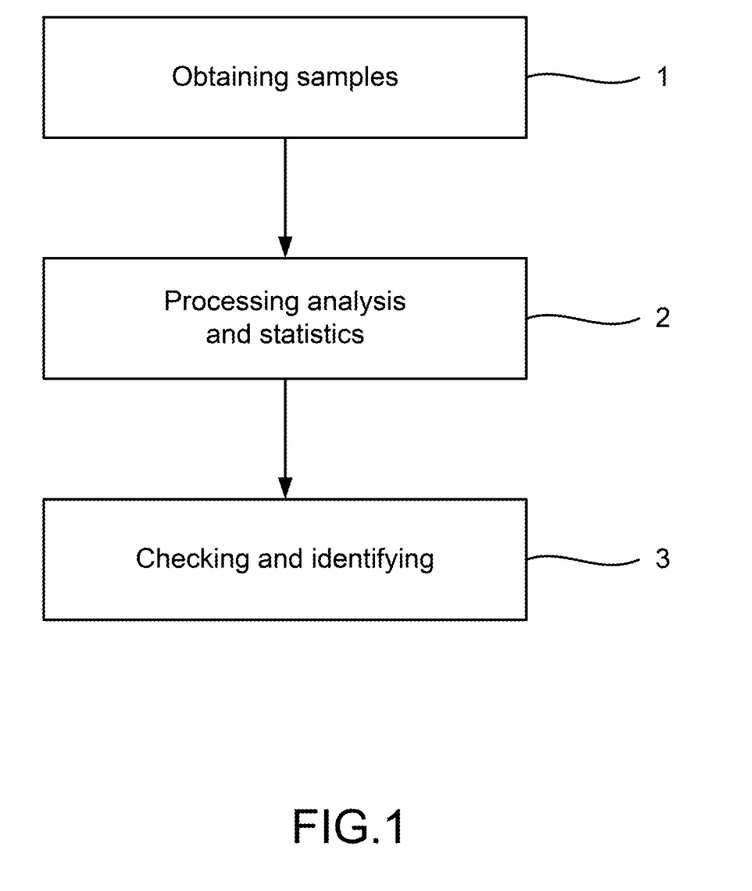
FIG. 1 is the flow view showing the preferred embodiment according to the present disclosure.

Please refer to FIG. 1, FIG. 2A to FIG. 2D, FIG. 3 to FIG. 6, FIG. 7A to FIG. 7B and FIG. 8A to FIG. 8B, which are a flow view showing the preferred embodiment according to the present disclosure; a view showing a result of mass spectrum image analysis; a view showing amino acid sequences of HNP1-3; a view showing distributions of HNP1-3; a view showing HNP-1 expression in a gastric cancer tissue through immunohistochemistry; a view showing HNP-1 expression in a gastric cancer tissue through western blotting; a view showing a standard HNP-1 curve; and a view showing a statistic result of HNP-1 expression in gastric cancer tissue obtained through SPSS. As shown in the figures, the present disclosure is a method of diagnosing gastric cancer by using human neutrophil peptide 1-3, comprising the following steps:

(a) Obtaining samples 1: Through an endoscopic operation or a surgical operation, a gastric cancer tissue and a normal gastric tissue are obtained as samples. Each sample has a 1 cubic-meter size and a 10 micrometers (um) thickness, which is put on an indium tin oxide (ITO) slide. The samples are dried to be fixed and to remove lipid with ethanol solutions having concentrations of 75%, 95% and 100% separately, where interference to a matrix assisted laser desorption ionization-time of flight mass spectrometer (MALDI-TOF MS) is thus avoided. MALDI-TOF MS is used to take photos of the gastric cancer tissue and the normal gastric tissue. Then, 4 points are used to decide spray area and spray amount, where 100 pL are sprayed in a 200 um area. At first, an OSV operation is processed for 20000 msec for cleaning with 150 uL of 100% methanol solution. After being fully cleaned, 5 times of cleaning for 1000 msec is processed. Then spraying is processed at a pressure between −0.3 and −0.6 kPa.

(b) Processing analysis and statistics 2: An analysis is processed to the gastric cancer tissue and the normal gastric tissue to obtain P values through statistics. Protein biomarkers having different expressions in between are distinguished with photos obtained through a general scanner to be saved for mass spectrum image analysis in a computer for MALDI-TOF/TOF. On taking photos of the slides, 3 points of white-out are dotted on the slides for observing statistic different expressions on processing the mass spectrum image analysis.

Then, western blotting is used to detect chemiluminescence. Tissue protein is added into a 500 uL lysis buffer to be grinded by a momogenizer; and, then, is processed through ultrasonics for 1 minutes (min). At a ratio of 1:1, sodium dodecyl sulfate buffer is added (50 mM Tris-Cl, 8M urea, 30% glycerol, 2% sodium dodecyl sulfate, 20 mM dithiothreitol and 0.1% bromophenol blue). After being boiled at 100 Celsius degrees (° C.) for 5 min to destroy protein binding bond, 4-12% sodium dodecyl sulfate-polyacrylamide gel electrophoresis (SDS-PAGE, Invitrogen) is used for electrophoresis analysis (at most 20 ug/lane is added). iblot (Invitrogen) is used to transfer protein on polyvinylidene fluoride (PVDF) to be reacted in a 3% de-fat milk for 30 min. Goat anti-HNP-1 polyclony antibodies (1:3000) are added for reaction at a room temperature for 1 hour. After being washed with a PBS buffer (10 mM sodium phosphate, pH7.4 and 0.9% sodium chloride) for 3 times, anti-goat antibody-HRP (1:3000) is added for reaction at a room temperature for 1 hour. After being washed with a PBS buffer for 3 times, ECL reagent (Millipore) is used for band observation to detect chemiluminescence with a LAS chemilumi/fluor system.

Then, immunohistochemistry is used for band observation. Stomach tissue is cut into 10 um thick by a cryotate (HM525, Microm) under −20° C. After being dried, the tissue is fixed and lipid of the tissue is removed by using 75%, 95% and 100% ethanol solutions. 3% $H_2O_2$ is added for reaction for 10 min to remove endogenous peroxidase activity. The tissue is boiled in a 10 mM citrate acid buffer for 25 min to uncover antigen. After being cooled down, the tissue is washed with a PBS buffer for 3 times. AEC kit (sigma) is used for reaction for 5~10 min for band observation. Then a microscope (BX51, Olympus) is used for observation.

At last, P values and related data are figured out through a non-denominator analytic method for Kruskal Wallis and Kendall's tau b.

Figure 2A:
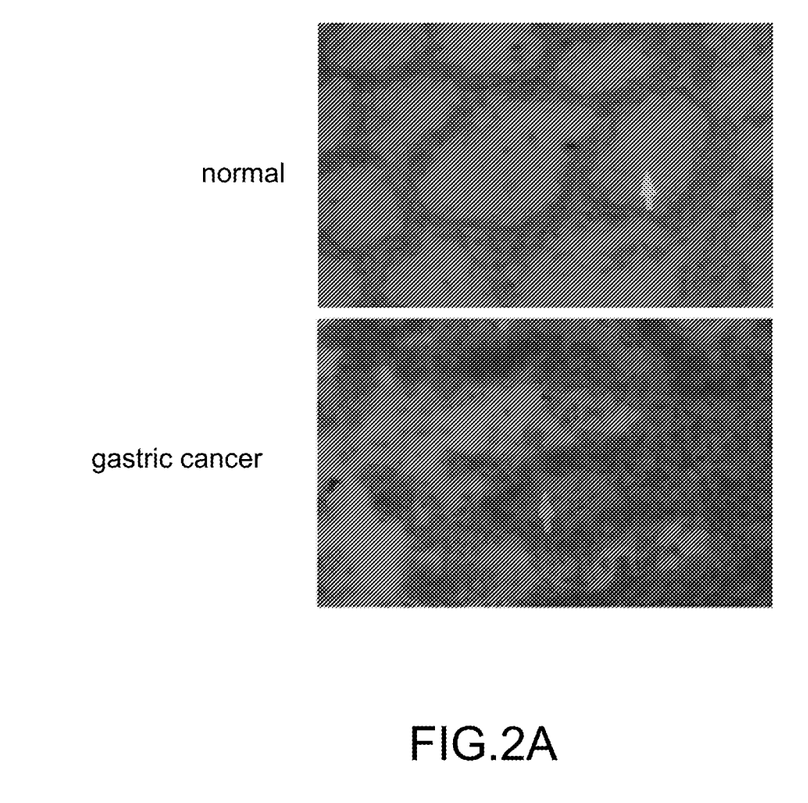
FIG. 2A to FIG. 2D are the views showing the results of mass spectrum image analysis.
Figure 2B:
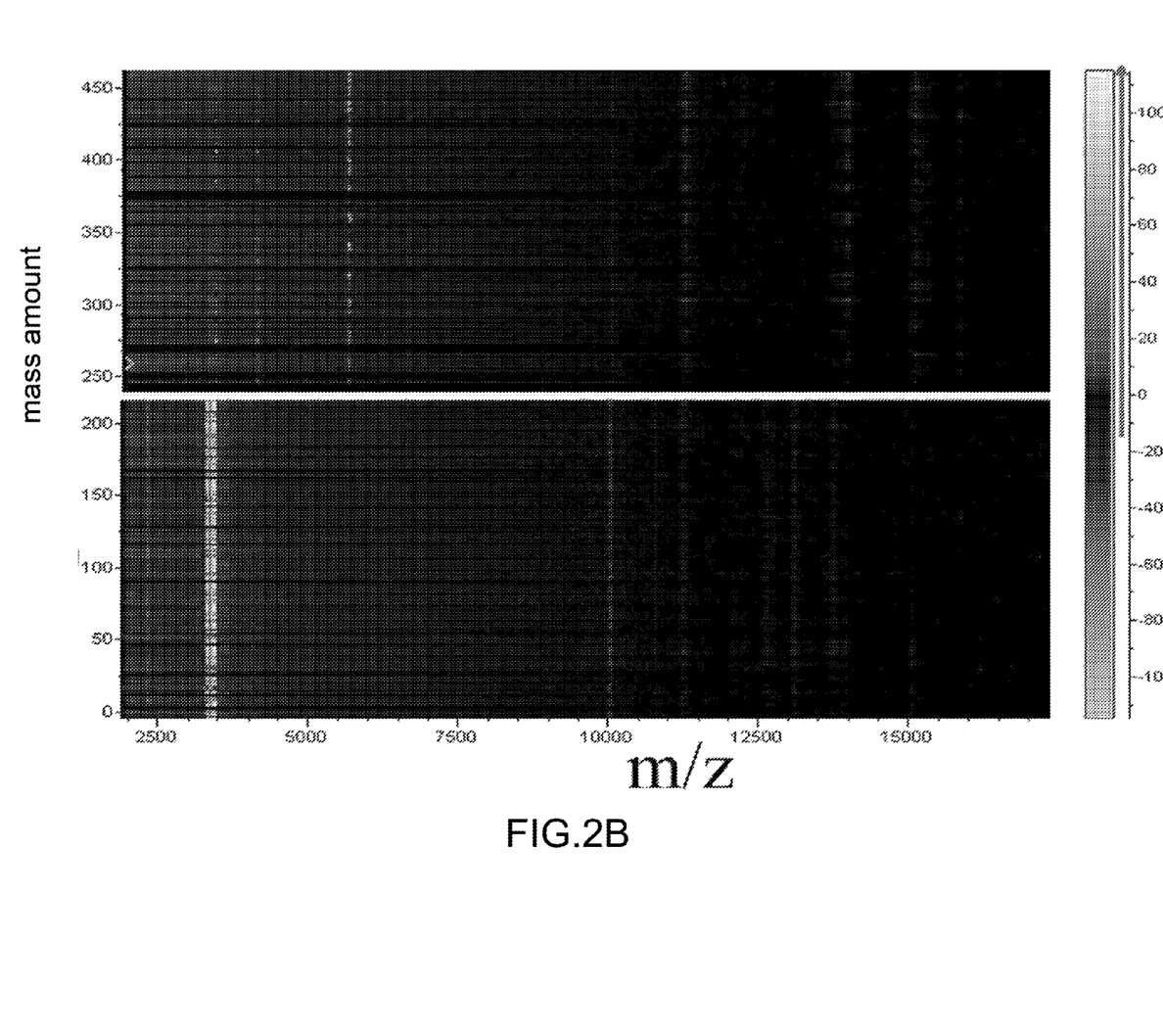
Figure 2C:
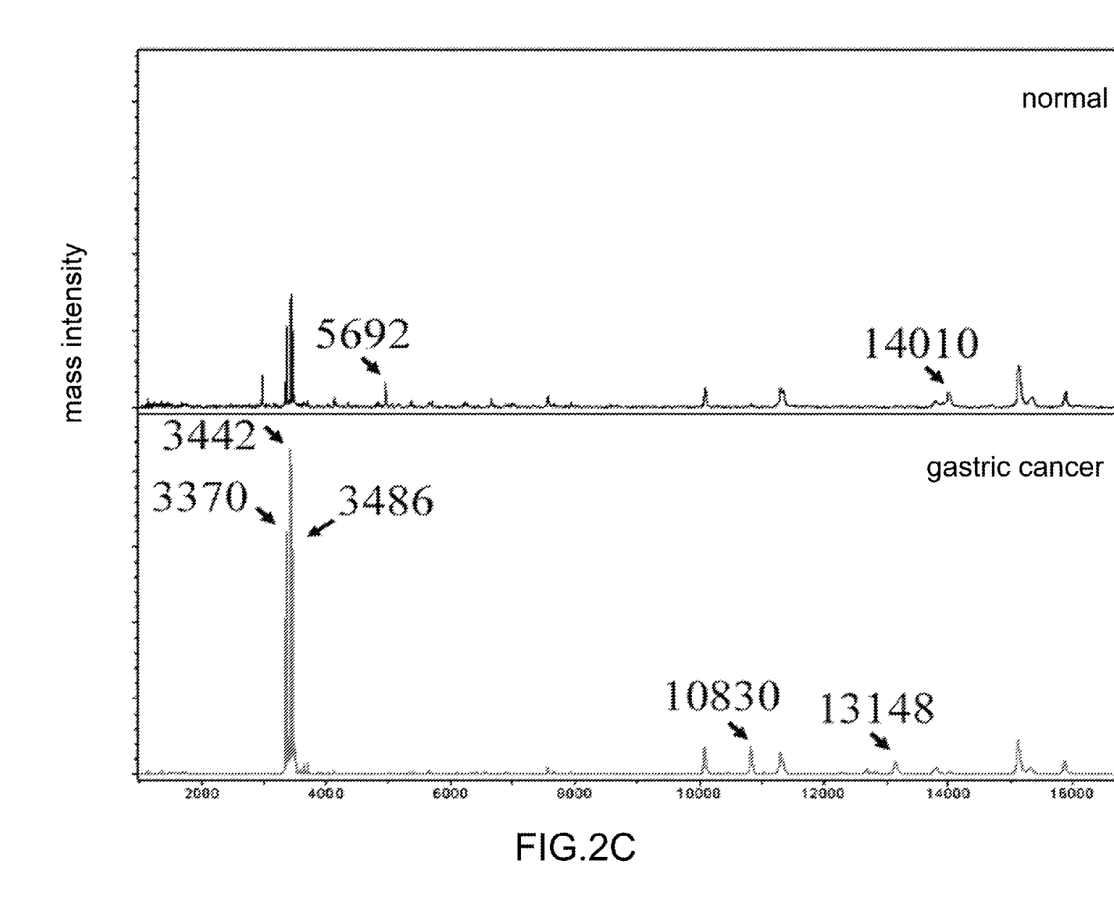
Figure 2D:
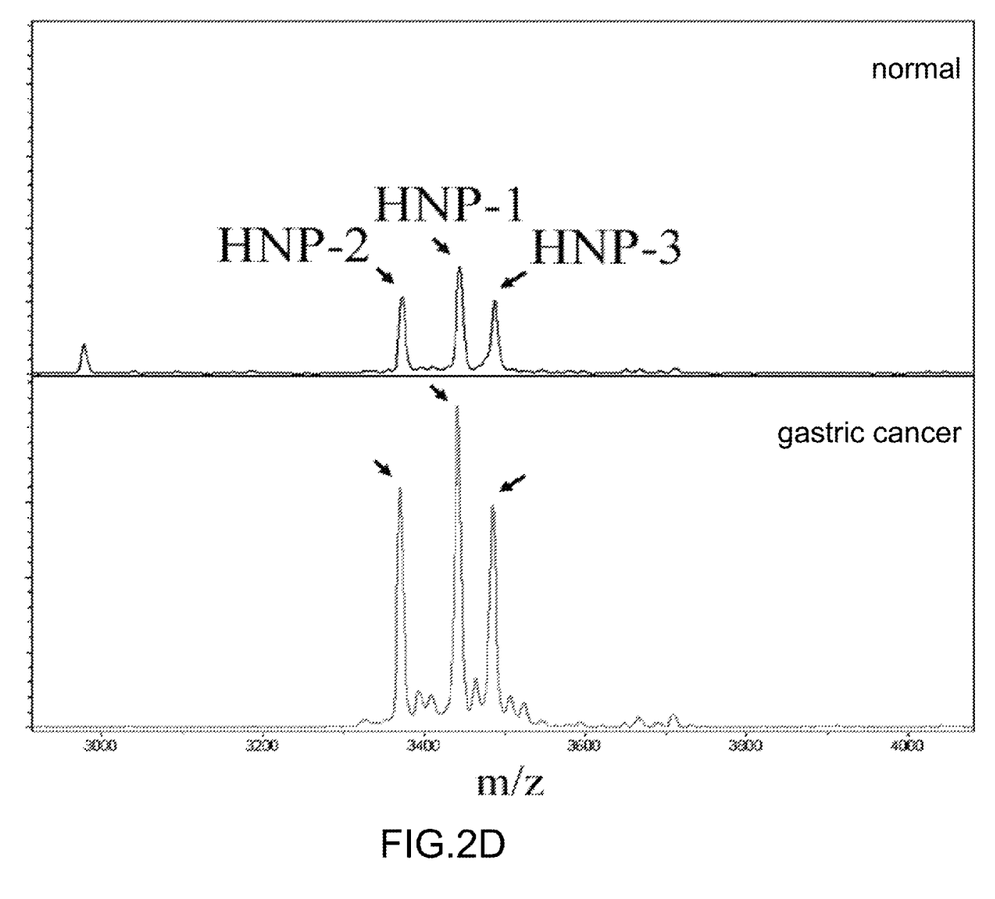
Figure 3:
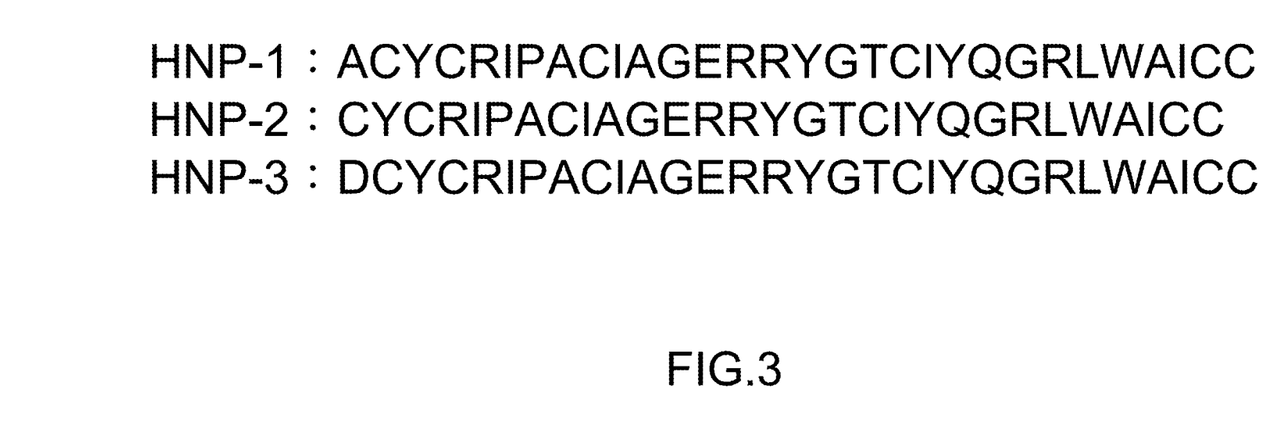
FIG. 3 is the view showing the amino acid sequences of HNP1-3; HNP1 (SEQ ID NO:2), HNP2 (SEQ ID NO:3), and HNP3 (SEQ ID NO:4)
Figure 4:
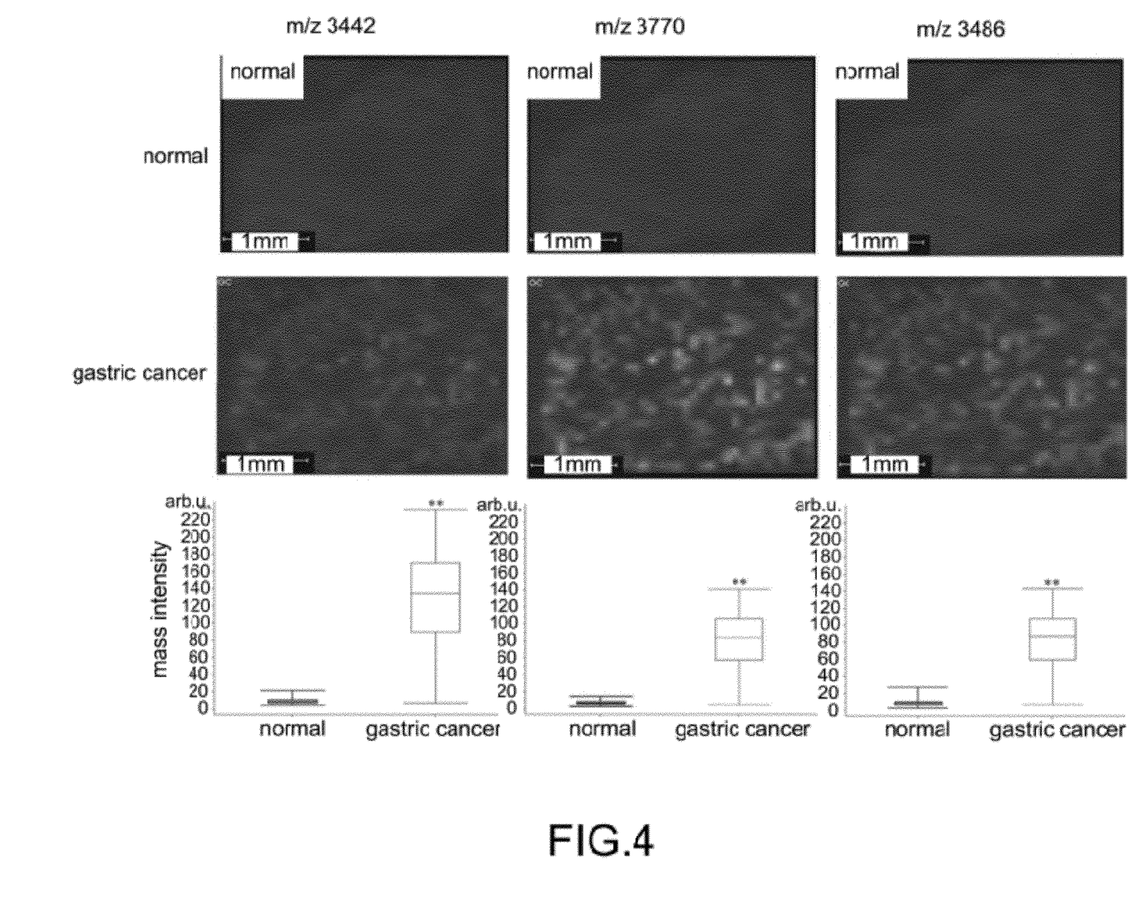
FIG. 4 is the view showing the distributions of HNP1-3.

(c) Checking and identifying 3: Through mass spectrum image analysis, two sequential tissues are identified. One is identified as a cell of a gastric cancer tissue through Methylene Blue staining (as shown in FIG. 2A). The other is combined with SA matrix through crystallization by using a matrix sprayer. After being detected through mass spectrum image analysis, numbers of some materials having molecule weights of 3370, 3442, 3486, 10830 and 13148 increase in the cancer tissue obviously; and numbers of some other materials having molecule weights of 5692 and 14010 decrease obviously (as shown in FIG. 2D). After checking those molecule weights, the molecule weights of 3370, 3442 and 3486 are respectively identified as HNP-1, HNP-2 and HNP-3, whose amino acid sequences has 1 amino acid residue on N end (as shown in FIG. 3). After being calculated through a statistic software 'ClinProt', data are transferred back to a software 'FlexImaging' for displaying image. It is then found that HNP-1, HNP-2 and HNP-3 are existed at the same place, which may mean they exist in or function on the same cell and may have the same function. Through Box-and-Whisker Plot, HNP-1, HNP-2 and HNP-3 are found to be expressed greatly in the gastric cancer tissue, where $P<0.01$ (as shown in FIG. 4).

Figure 5:
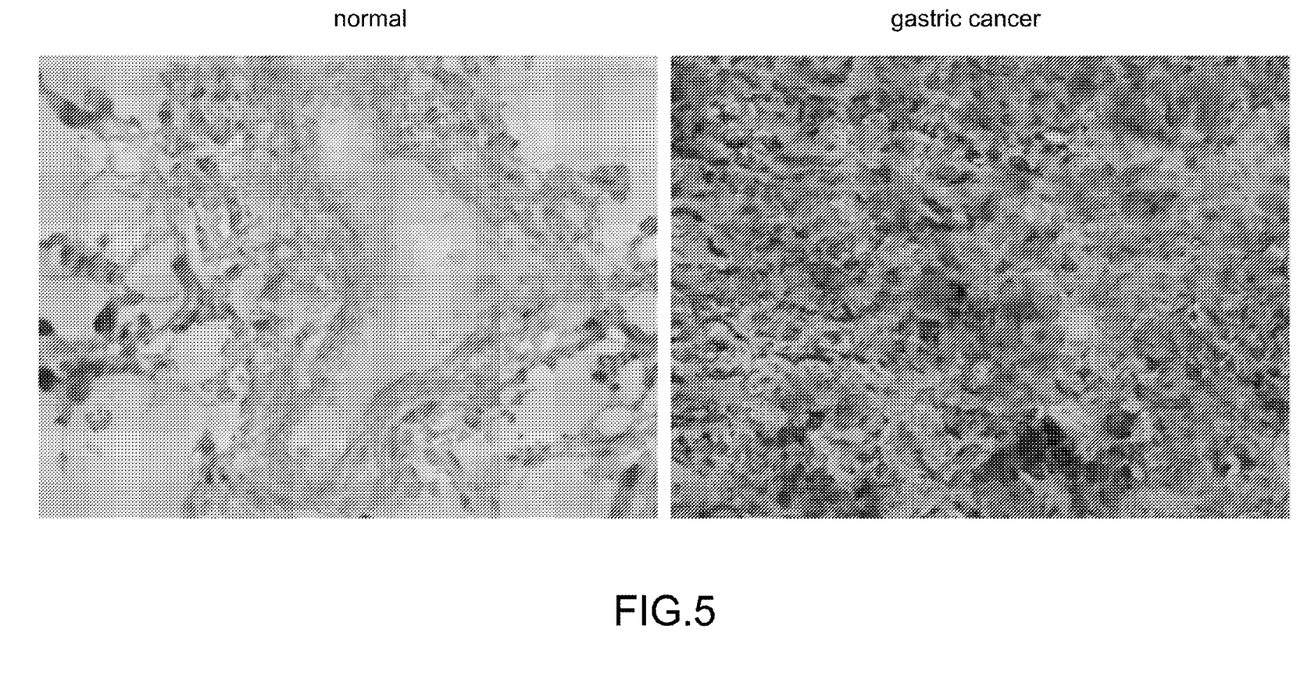
FIG. 5 is the view showing the HNP-1 expression in the gastric cancer tissue through immunohistochemistry.
Figure 6:
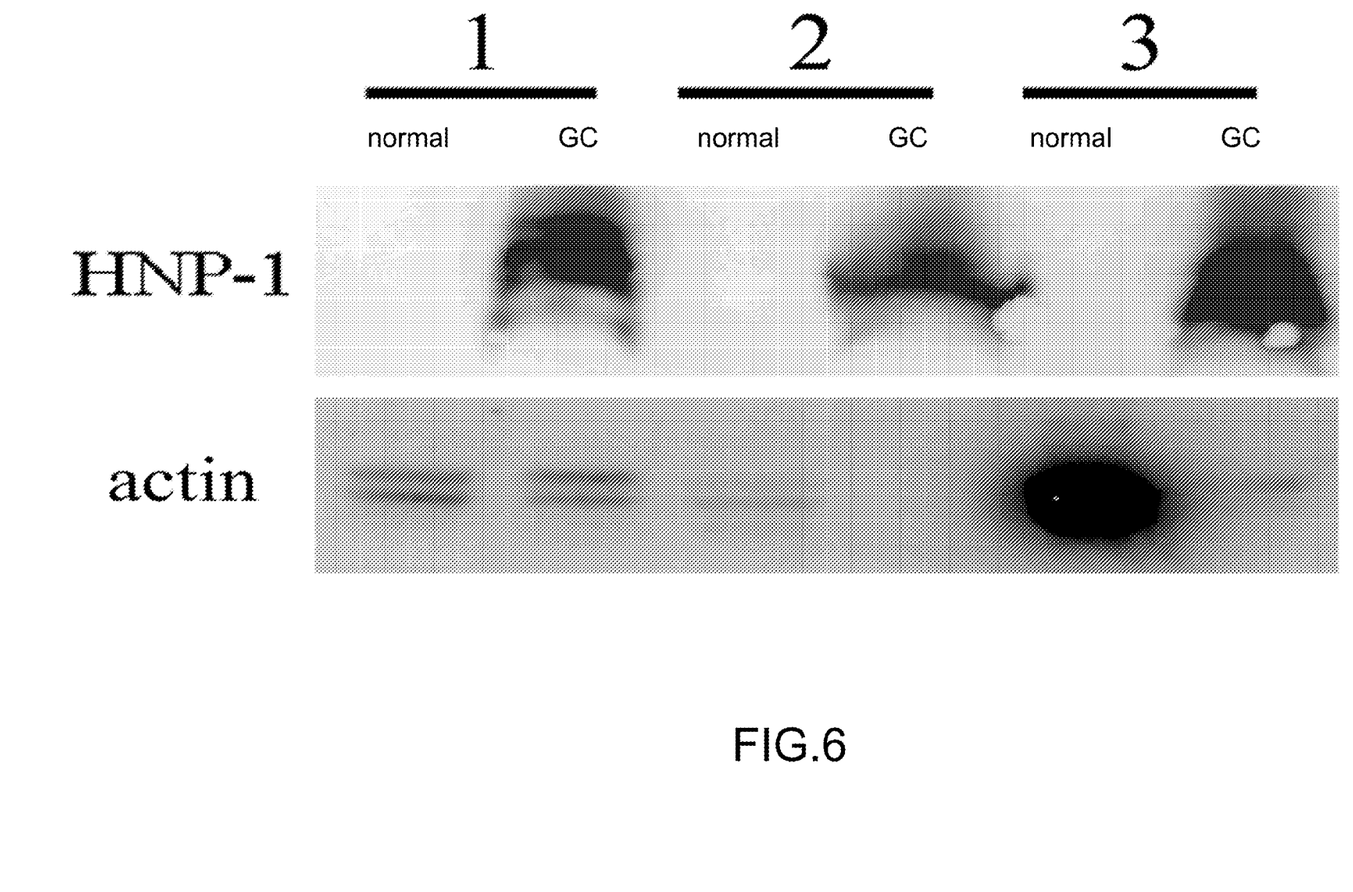
FIG. 6 is the view showing the HNP-1 expression in the gastric cancer tissue through western blotting.

Then, HNP-1 is checked for its expression on immunity, where western blotting and immunohistochemistry are used to acquire expression of HNP-1 in the gastric cancer tissue by using a specific antibody of HNP-1. Through immunohistochemistry, HNP-1 shows more expression in the gastric cancer tissue than that in the normal gastric tissue, which is mainly expressed in gastric adenocarcinorma (as shown in FIG. 5). Through western blotting, HNP-1 is found mainly existed in the gastric cancer tissue (as shown in FIG. 6) while almost not found in the normal gastric tissue.

Figure 7A:
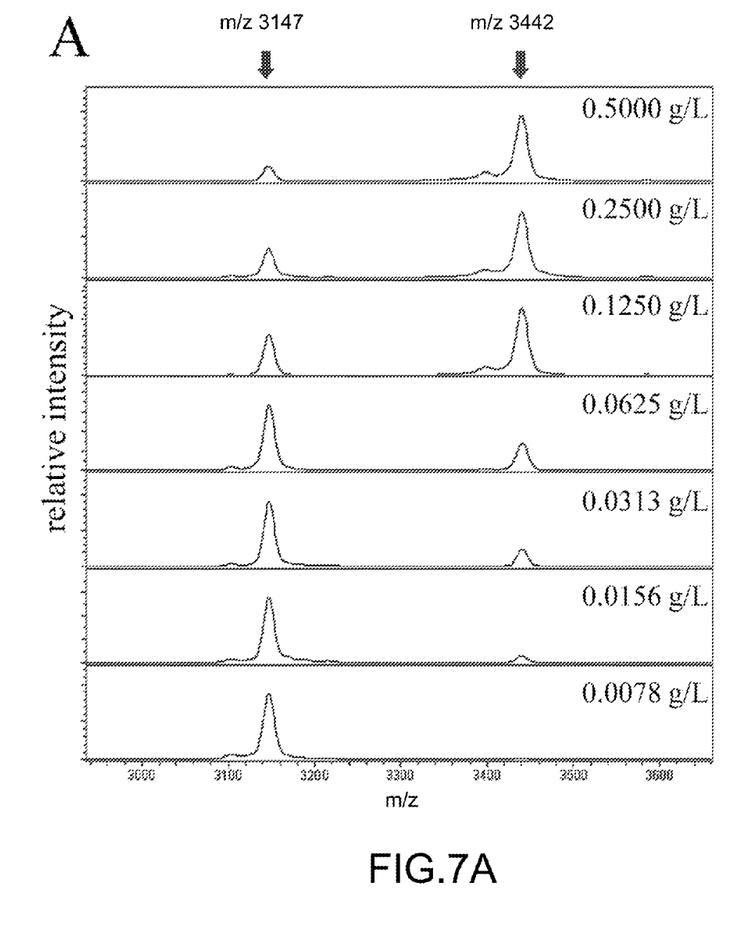
FIG. 7A and FIG. 7B are the views showing the standard HNP-1 curve.
Figure 7B:
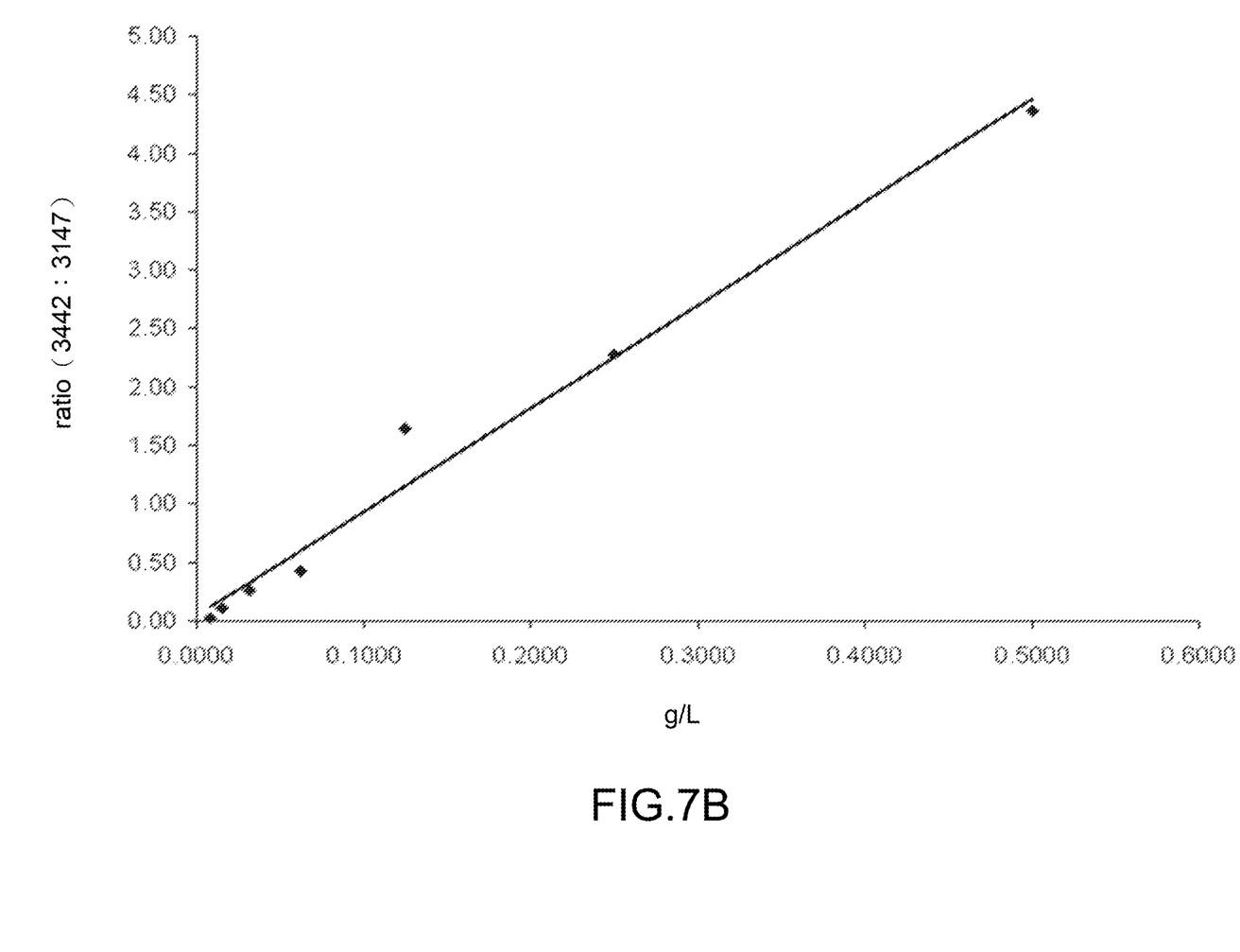

Then, MALDI-TOF is used for quantification of extraction of the gastric cancer tissue. At first, a standard curve for pure HNP-1 protein is obtained. Seven solutions of 0.5 mg/mL HNP-1 are diluted into 0.5, 0.25, 0.125, 0.0625, 0.0313, 0.0156 and 0.0078 mg/mL separately. After adding a standard peptide solution (having a ratio of 1:1), a same amount of 20 mg/mL SA matrix are added to be mixed for crystallization. In FIG. 7, a standard curve is obtained with a ratio (y) of molecule weights of 3442 and 3147 and a concentration (x) of HNP-1, whose related coefficient (r2) is 0.9802 and a function of the concentration (x) and the ratio (y) is thus obtained as y=8.8409x+0.0479.

Figure 8A:
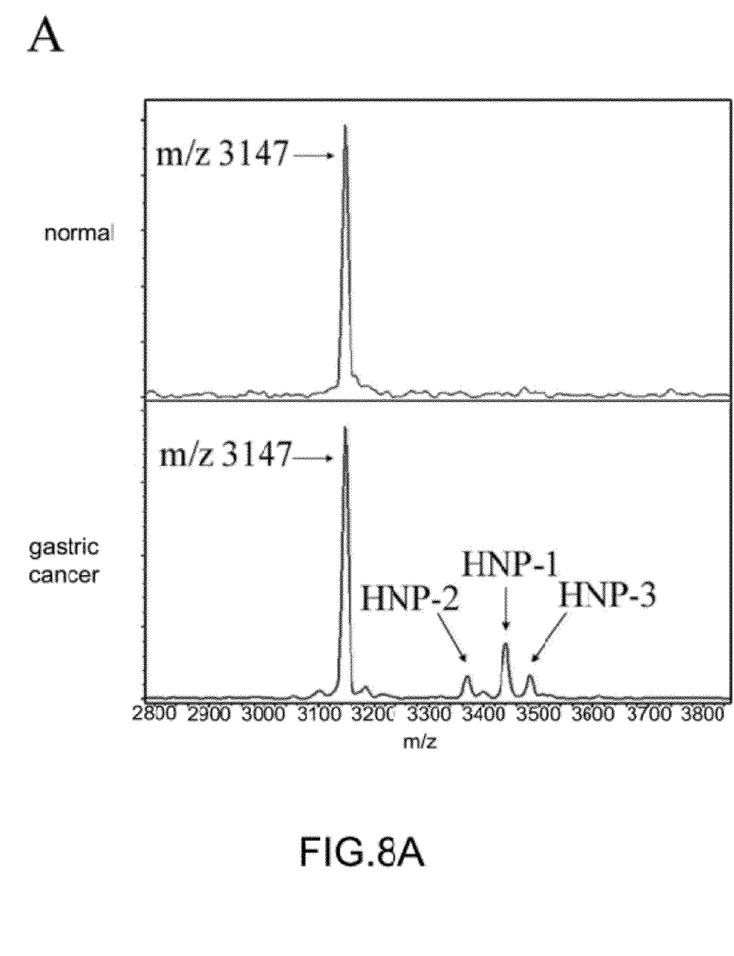
FIG. 8A and FIG. 8B are the views showing the statistic result of HNP-1 expression in the gastric cancer tissue obtained through SPSS.
Figure 8B:
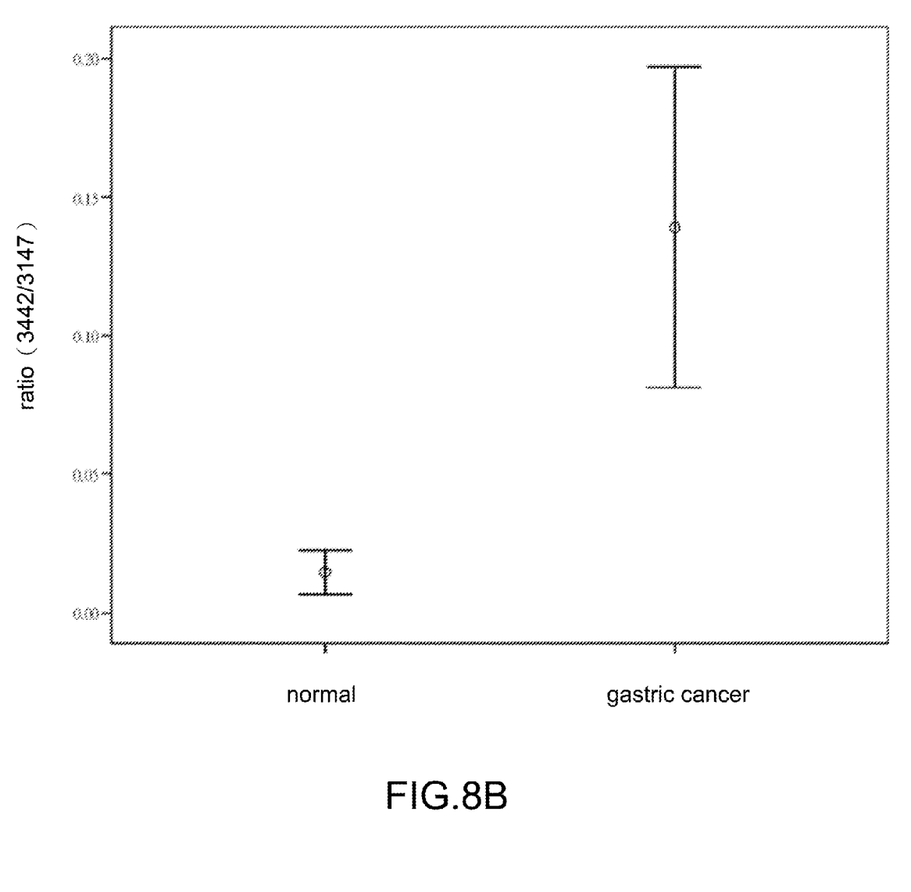

In 20 pairs of normal gastric cancer tissue and gastric cancer tissue, 10 ul of 50% Acetonitrile/0.1% Trifluoroacetic acid is added per 1 mg for protein extraction to be reacted on a shaker for 1 hour. When a result value is '0', no signal for HNP-1 is shown. The concentration is figured out through the function y=8.8409x+0.0479. The pairs of normal gastric cancer tissue and gastric cancer tissue are mixed with peptide and matrix to be analyzed through MALDI-TOF MS. It is found that HNP1-3 is greatly expressed in the gastric cancer tissues. Through processing statistics by using SPSS, HNP-1 in the extraction of normal gastric tissue is about 0.01±0.008 mg/mL; and that in the extraction of gastric cancer tissue is about 0.14±0.058 mg/mL (P<0.03) (as shown in FIG. 8).

The HNP1-3 are anti-bacteria and anti-virus peptide from Granulocytes, (i.e. polymorphonuclear leukocytes, PMN or PML) according to the present disclosure. HNP1-3 are not only found in gastric cancer tissue but also in succus gastricus of a helicobacter pylori patient. Moreover, HNP1-3 are found in other malignant tumor, like colonrectal cancer, oral cancer, bladder cancer, etc. HNP1-3 are three sections peptide which differs in one aminoacid at N end. Through mass spectrum image analysis, HNP1-3 are found at the same position, which may mean they have the same functions or exist in the same cell. HNP1-3 are not only expressed in solid tissue but also serum. Hence, HNP1-3 are suitable to be used as protein biomarkers of gastric cancer or other malignant tumor, which may be further developed into a serum diagnostic kit or a nuclear imaging reagent.

To sum up, the present disclosure is a method of diagnosing gastric cancer by using HNP1-3, where HNP1-3 are used for diagnosing gastric cancer with specificity and sensitivity and hence gastric cancer can be diagnosed for treatment at an early stage.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A method of diagnosing gastric cancer by using human neutrophil peptide (HNP) 1-3, comprising the steps of:
   (a) obtaining samples consisting of a gastric tissue from a patient and a normal gastric tissue;
   (b) determining the amount of protein biomarkers HNP1, HNP2 and/or HNP3 in the samples using MALDI-TOF mass spectrometry; wherein said three protein biomarkers have molecular weights of 3370(HNP1), 3442(HNP2) and 3486(HNP3); and
   (c) diagnosing a gastric cancer at an early stage if the amount of each biomarker in the patient sample is higher than the amount in normal sample.

2. The method according to claim 1, wherein, in step (a), said sample is obtained through an operation selected from a group consisting of an endoscopic operation and a surgical operation.

3. The method according to claim 1, wherein, in step (a), said sample has a 1 cubic-meter size and is obtained on an indium tin oxide (ITO) slide; and ethanol solutions are used to dry and fix said sample and to remove lipid contained in said sample; and wherein said ITO slide has a thickness of 10 micrometers (um) and said ethanol solutions have concentrations of 75%, 95% and 100% separately.

* * * * *

SEQUENCE LISTING

<160> NUMBER OF SEQ ID NOS: 4

<210> SEQ ID NO 1
<211> LENGTH: 514
<212> TYPE: DNA
<213> ORGANISM: Homo sapiens

<400> SEQUENCE: 1

```
ggctgctcct tgctatagaa gacctgggac agaggactgc tgtctgccct ctctggtcac    60
cctgcctagc tagaggatct gtgacccag ccatgaggac cctcgccatc cttgctgcca   120
ttctcctggt ggccctgcag gcccaggctg agccactcca ggcaagagct gatgaggttg   180
ctgcagcccc ggagcagatt gcagcggaca tcccagaagt ggttgtttcc cttgcatggg   240
acgaaagctt ggctccaaag catccaggct caaggaaaaa catggcctgc tattgcagaa   300
taccagcgtg cattgcagga gaacgtcgct atggaacctg catctaccag ggaagactct   360
gggcattctg ctgctgagct tgcagaaaaa gaaaaatgag ctcaaaattt gctttgagag   420
ctacagggaa ttgctattac tcctgtacct tctgctcaat ttcctttcct catcccaaat   480
aaatgccttg ttacaagaaa aaaaaaaaaa aaaa                               514
```

<210> SEQ ID NO 2
<211> LENGTH: 30
<212> TYPE: PRT
<213> ORGANISM: Artificial sequence
<220> FEATURE:
<223> OTHER INFORMATION: HNP-1 peptide

<400> SEQUENCE: 2

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Ile Cys Cys
            20                  25                  30

<210> SEQ ID NO 3
<211> LENGTH: 29
<212> TYPE: PRT
<213> ORGANISM: Artificial sequence -continued

```
<220> FEATURE:
<223> OTHER INFORMATION: HNP-2 peptide

<400> SEQUENCE: 3

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Ile Cys Cys
            20                  25

<210> SEQ ID NO 4
<211> LENGTH: 30
<212> TYPE: PRT
<213> ORGANISM: Artificial sequence
<220> FEATURE:
<223> OTHER INFORMATION: HNP-3 peptide

<400> SEQUENCE: 4

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Ile Cys Cys
            20                  25                  30
```